United States Patent [19]

Pastour et al.

[11] Patent Number: 5,523,091

[45] Date of Patent: Jun. 4, 1996

[54] USEFUL COSMETIC OR PHARMACEUTICAL WATER-IN-OIL EMULSION

[75] Inventors: Valérie Pastour, Suresnes; Françoise Pouget, Fontenay Sous Bois; Pierre Fodor, Garches, all of France

[73] Assignee: L'Oreal, Paris, France

[21] Appl. No.: 198,057

[22] Filed: Feb. 18, 1994

[30] Foreign Application Priority Data

Feb. 23, 1993 [FR] France .................................. 93 02048

[51] Int. Cl.$^6$ ...................................................... A61K 7/02
[52] U.S. Cl. .............................. 424/401; 424/56; 424/63; 514/844; 514/937
[58] Field of Search ............................... 424/401, 56, 63; 514/844, 845, 846, 847, 937, 947

[56] References Cited

U.S. PATENT DOCUMENTS

| | | | |
|---|---|---|---|
| 5,015,469 | 5/1991 | Yoneyama et al. | 424/59 |
| 5,196,187 | 3/1993 | Nicoll et al. | 424/70 |
| 5,210,251 | 5/1993 | Ohashi et al. | 556/437 |
| 5,266,321 | 11/1993 | Shukuzaki et al. | 424/401 |
| 5,362,482 | 11/1994 | Yoneyama et al. | 424/69 |
| 5,412,004 | 5/1995 | Tachibana et al. | 524/27 |

FOREIGN PATENT DOCUMENTS

| | | |
|---|---|---|
| 0374332 | 6/1990 | European Pat. Off. . |
| 374332 | 6/1990 | European Pat. Off. . |
| 2686510 | 7/1993 | France . |
| 9314742 | 8/1993 | WIPO . |

*Primary Examiner*—John C. Bleutge
*Assistant Examiner*—Robert H. Harrison

[57] ABSTRACT

A cosmetic or pharmaceutical water-in-oil emulsion composition, exhibiting time and temperature stability, comprises in an aqueous phase, (a) a fatty phase comprising (i) a silicone and (ii) a gelling agent and (b) an emulsifying agent. The fatty phase is present in an amount ranging from 15 to 40 weight percent of the emulsion and contains 10 to 90 weight percent of the (i) silicone and 0.1 to 5 percent of the (ii) gelling agent. The emulsifying agent is present in an amount ranging from 0.5 to 10 percent by weight.

10 Claims, No Drawings

USEFUL COSMETIC OR PHARMACEUTICAL WATER-IN-OIL EMULSION

The subject of the present invention is water-in-oil (W/O) emulsions for cosmetic or pharmaceutical use which have a high silicone content.

Such W/O emulsions are useful in cosmetics especially for their ability to form films at the surface of the skin which efficiently prevent loss of water through the skin and give good resistance to infections by microorganisms.

It is known that as the silicone oil content increases, it becomes more difficult to obtain a W/O emulsion which is stable not only with time but also when it is subjected to significant temperature variations.

This stability problem could be at least partially resolved, according to U.S. Pat. No. 4,698,178, by the use of a new class of silicone-containing surface-active agents in combination with polyols for low temperatures and with electrolytes or metal salts for high temperatures.

Stabilization of W/O emulsions was also achieved, according to application EP 331,833, by the use of silicone-containing surface-active agents in combination with water-swellable inorganic clays or, according to application EP 374,332, by the use of waxes.

It has now been found, unexpectedly and surprisingly, that, by the use of a class of specific gelling agents of the fatty phase, it was possible to obtain W/O emulsions which have good stability not only with time but also with respect to temperature variations.

The subject of the present invention is thus a stable water-in-oil emulsion, for cosmetic or pharmaceutical use, consisting of a fatty phase containing a silicone, of a non-gelled aqueous phase and of an emulsifying agent chosen from an alkyl- or alkoxydimethicone copolyol or a dimethicone copolyol, or their mixtures, characterized in that the fatty phase represents from 15 to 40% by weight of the total weight of the emulsion, the said fatty phase consisting of at least 10 to 90% by weight of silicone and of 0.1 to 5% of a gelling agent consisting of a mixture of fatty acid esters of glycerol and of glycol in a ratio of between 75/25 and 95/5% by weight, the said fatty acids being $C_{16}-C_{36}$ and at least 50% of the said fatty acids being $C_{18}-C_{22}$.

The W/O emulsion according to the invention corresponds entirely to the stability standards, i.e.:
- resistance to the centrifuging test at 4000 rev/min for 1 hour,
- resistance to aging at room temperature for 3 months as well as at 45° C. and at +4° C., and
- resistance to 8 successive cycles of 8 hours each in which the temperatures range from −20° C. to +20° C.

The emulsion according to the invention corresponds to the following criteria:
- it has, and retains during these tests, a homogeneous and stable macroscopic and microscopic appearance (finely dispersed globules, absence of growth) and
- its viscosity is constant over time.

Moreover, the emulsion according to the invention has good sensory qualities, especially great ease of application, comfort, softness, good mattness, uniformity and hold. Its preparation is facilitated by the use of the gelling agent.

Mention may be made, among gelling agents which can be used according to the invention and which correspond to the definition given above, of especially the product sold under the name of "UNITWIX®" by the Company United Guardian.

This product consists essentially of approximately 85% by weight of glycerol esters and 15% by weight of glycol esters. It has a melting point of approximately 68°–70° C. and the $C_{18}-C_{22}$ fatty acids content is between approximately 60 and 65%.

The emulsifying agent according to the invention is an alkyl- or alkoxydimethicone copolyol or a dimethicone copolyol of general formula:

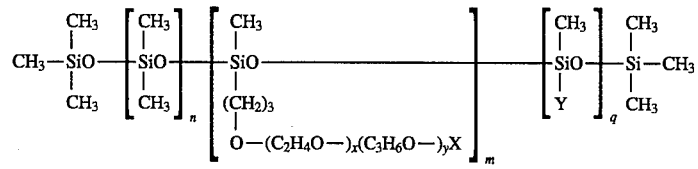

in which:

X is a hydrogen atom or a $C_1-C_{16}$ acyl, alkoxy or alkyl,

Y is a $C_8$ to $C_{22}$ alkoxy or alkyl radical, n=0 to 200, m=1 to 40, q=0 to 100, the molecular weight of the $(C_2H_4O-)_x(C_3H_6O-)_y-X$ residue being from 250 to 2000, x and y being chosen so that the ratio by weight of the oxyethylene/oxypropylene groups is between 100:0 and 20:80.

The surface-active or emulsifying agent as defined above is used according to the invention in a proportion of between 0.5 and 10%, preferably between 2 and 6%, by weight with respect to the total weight of the emulsion and has proved to be less irritating than certain other surface-active agents.

Mention may be made, among commercially available products which can contain all or part of the alkyldimethicone copolyols which can be used according to the invention as emulsifying agent, of especially those sold under the names "ABIL WE09®" or "ABIL WS08®" or "ABIL EM90®" by the Company Goldschmidt, "Q2 5200®" by the Company Dow Corning and "218-1138®" by the Company General Electric.

Mention may be made, among commercially available products which can contain all or part of the dimethicone copolyols which can be used according to the invention, of especially that sold under the name "SF1228®" by the Company General Electric.

The silicone which can be used according to the invention can be a cyclic or, optionally functionalized, linear polydiorganosiloxane or an optionally crosslinked organopolysiloxane or a mixture of these.

The optionally functionalized linear polydiorganosiloxanes which can be used according to the invention correspond to the following general formula:

$$X-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_n-\underset{\underset{CH_3}{|}}{\overset{\overset{CH_3}{|}}{Si}}-X$$

in which

X is —$CH_3$ or OH, and n is 0 to 5000.

Mention will be made, among the latter, of especially the products sold under the name "AK®" by the Company Wacker, "SF®" by the Company General Electric and "ABIL®" by the Company Goldschmidt, such as the product "ABIL 10®", or else the products sold under the name "Q2 1401®" and "Q2 1403®" by the Company Dow Corning.

It is possible to use, as cyclic polydiorganosiloxanes according to the invention, alone or as mixtures, cyclomethicones of formula:

$$\left[\underset{\underset{CH_3}{|}}{\overset{\overset{CH_3}{|}}{Si}}-O\right]_n$$

in which n is an integer from 3 to 8.

Mention will be made, among particularly preferred cyclomethicones, of cyclotetradimethylsiloxane (n=4), cyclopentadimethylsiloxane (n=5) and cyclohexadimethylsiloxane (n=6).

It is possible especially to use the products sold under the names of "DC FLUID 244®", "DC FLUID 245®", "DC FLUID 344®" and "DC FLUID 345®" by the Company Dow Corning.

Other cyclomethicones which can be used according to the invention are those sold under the names "ABIL K4®" by the Company Goldschmidt; under the names "SILBIONE 70045 V2®" and "SILBIONE HUILE 70045 V5®" by the Company Rhône-Poulenc; and under the names "VOLATIL SILICONE 7158®" and "VOLATIL SILICONE 7207®" by the Company Union Carbide.

The organopolysiloxanes according to the invention can be alkyl-, alkoxy- or phenyldimethicones such as, for example:

(a) an alkoxydimethicone having one of the following formulae:

$$R-O-\left[\underset{\underset{CH_3}{|}}{\overset{\overset{CH_3}{|}}{Si}}-O\right]_m-\left[\underset{\underset{CH_3}{|}}{\overset{\overset{CH_3}{|}}{Si}}-O\right]_n-\underset{\underset{CH_3}{|}}{\overset{\overset{CH_3}{|}}{Si}}-O-R$$

or $$CH_3-\underset{\underset{CH_3}{|}}{\overset{\overset{CH_3}{|}}{Si}}-O-\left[\underset{\underset{OR}{|}}{\overset{\overset{CH_3}{|}}{Si}}-O\right]_m-\left[\underset{\underset{CH_3}{|}}{\overset{\overset{CH_3}{|}}{Si}}-O\right]_n-\underset{\underset{CH_3}{|}}{\overset{\overset{CH_3}{|}}{Si}}-CH_3$$

in which:

R is a $C_6$ to $C_{30}$ alkyl radical m is 1 to 100, and n is 0 to 100.

Mention may in particular be made of the product sold under the name "ABIL WAX 2440®" by the Company Goldschmidt.

(b) an alkyldimethicone having one of the following formulae:

$$CH_3-\underset{\underset{CH_3}{|}}{\overset{\overset{CH_3}{|}}{Si}}-O-\left[\underset{\underset{R}{|}}{\overset{\overset{CH_3}{|}}{Si}}-O\right]_m-\left[\underset{\underset{CH_3}{|}}{\overset{\overset{CH_3}{|}}{Si}}-O\right]_n-\underset{\underset{CH_3}{|}}{\overset{\overset{CH_3}{|}}{Si}}-CH_3$$

in which:

R is a $C_6$ to $C_{30}$ alkyl radical, m is 1 to 100 and n is 0 to 100, or $$R-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_m-\underset{\underset{CH_3}{|}}{\overset{\overset{CH_3}{|}}{Si}}-R$$

in which:

R is a $C_6$ to $C_{30}$ alkyl radical, and m is 1 to 100.

(c) a phenyldimethicone having the following formula:

$$CH_3-\underset{\underset{CH_3}{|}}{\overset{\overset{CH_3}{|}}{Si}}-O-\left[\underset{\underset{O-Si(CH_3)_2-CH_3}{|}}{\overset{\overset{C_6H_5}{|}}{Si}}-O\right]_n-\left[\underset{\underset{CH_3}{|}}{\overset{\overset{CH_3}{|}}{Si}}-O\right]_m-\underset{\underset{CH_3}{|}}{\overset{\overset{CH_3}{|}}{Si}}-CH_3$$

in which:

m is 0 to 100 and n is 1 to 400 or the following formula:

$$CH_3-\underset{\underset{CH_3}{|}}{\overset{\overset{CH_3}{|}}{Si}}-O-\left[\underset{\underset{C_6H_5}{|}}{\overset{\overset{C_6H_5}{|}}{Si}}-O\right]_n-\underset{\underset{CH_3}{|}}{\overset{\overset{CH_3}{|}}{Si}}-CH_3$$

in which:

n is 0 to 400.

The silicones which can be used according to the invention can also be silicone resins comprising a combination of the units:

$R_3SiO_{1/2}$, $R_2SiO_{2/2}$, $RSiO_{3/2}$ and $SiO_{4/2}$,

R being a $C_1$ to $C_6$ lower alkyl or phenyl radical.

As mentioned above, the silicone used according to the invention is present in a proportion of at least 10% and preferably of between 20 and 90%, by weight with respect to the weight of the fatty phase.

The fatty phase of the W/O emulsion according to the invention can comprise one or more hydrocarbon oil(s) in a proportion of between 0.1 and 52% by weight with respect to the total weight of the fatty phase of the emulsion.

Mention will be made, as hydrocarbon oil, of: any fluid oil (or mixture of oils) which is stable at the usual temperature of use of cosmetic products and which is pharmaceutically or cosmetically acceptable, such as vegetable or animal oils, mineral or synthetic oils, fluorinated oils and triglycerides of $C_{12}$–$C_{18}$ fatty acids.

Mention may be made, among modified or unmodified vegetable or animal oils, of, for example, sweet almond oil, avocado oil, castor oil, olive oil, jojoba oil, sunflower oil, wheat germ oil, sesame oil, groundnut oil, grape seed oil, soya oil, rapeseed oil, safflower oil, coconut oil, maize oil, hazelnut oil, karite butter, palm oil, apricot kernel oil or calophyllum oil.

Mention may be made, among mineral oils, of, for example, liquid paraffin.

Mention may be made, among synthetic oils, of especially isoparaffins and polyisobutenes.

According to a specific embodiment, the emulsion according to the invention can also comprise an additional surface-active agent such as a glycerol ether or ester and/or an oxyethylenated polydimethylsiloxane dispersion in a cyclodimethylsiloxane ("Q3225C®" of the Company Dow Corning), having an HLB of between 2 and 7 and present in a proportion of between 0.01 and 5% by weight with respect to the total weight of the emulsion.

Mention may be made, among additional surface-active agents of this type, of the esters or ethers of glycerol, especially the isostearic acid ester and/or the succinic acid ester and the decyltetradecyl alcohol ether. Mention may be made, for example, of the product sold by the Company Hüls under the name "IMWITOR 780K®", which is an isostearyl diglyceryl succinate.

Moreover, there are commercially available certain products consisting of a mixture of alkyldimethicone copolyol of the formula given above and of an additional surface-active agent of the type mentioned above.

Mention will be made, in this respect, of the product sold by the Company Goldschmidt under the name "ABIL WE09®", which contains an alkyldimethicone copolyol containing a ratio by weight of oxyethylene/oxypropylene groups of between 100:0 and 20:80, in combination with a glyceryl isostearate and hexyl laurate.

According to the invention, the fatty phase can also contain pigments optionally coated with hydrophilic or hydrophobic substances such as:

polyethylene, lecithin, an amino acid salt such as aluminum acylglutamate, poly(methyl methacrylate), triisostearoyltitanate, and collagen.

Mention may be made, among coated pigments, of especially the pigments sold under the name "COVASIL®" by the Company Wacker (pigments containing triisostearoyltitanate).

The pigments thus coated can be incorporated in the emulsion according to the invention in a proportion of between 0.1 and 15% by weight with respect to the total weight of the emulsion.

Mention may be made, among other liposoluble adjuvants which can be incorporated in the fatty phase, of lipophilic U.V. screening agents, lipophilic vitamins, antioxidizing agents and fragrances, and ceramides.

The aqueous phase can also contain adjuvants commonly used in cosmetic W/O emulsions. Mention will be made, for example, of lubricating agents, hydrating agents, such as glycerol and propylene glycol, trace elements, hydrophilic U.V. screening agents, polysaccharides and electrolytes such as NaCl or $MgSO_4$. It can also comprise active principles such as plant extracts, bacterial extracts, proteins or their hydrolysates and especially elastin or collagen hydrolysates.

These active principles are then present in a proportion of between 1 and 15%.

The emulsion according to the invention can also incorporate fillers of plant, inorganic or synthetic origin, in particular starch powder, colloidal silica, nylon powder (Orgasol) and talc.

The emulsions according to the invention can be in the form of a white or colored cream, in the form of a milk or in the form of a foundation cream, mascara, blusher or a make-up product for the lips.

The process for the preparation of the emulsions according to the invention consists: (a) in a first step, in heating the fatty phase containing the emulsifying agent and the gelling agent to a temperature sufficient to melt all the constituents, preferably between 60° and 85° C., and in then incorporating therein the optional additional liposoluble adjuvants and (b) in a second step, after cooling the fatty phase to between 40° and 60° C., in slowly adding the aqueous phase, brought to the same temperature, to the fatty phase with gentle stirring and then, when the temperature has returned to approximately 25° C., in then subjecting the preparation to vigorous stirring.

This second stage can also be carried out by addition of the aqueous phase to the fatty phase with vigorous stirring, the aqueous phase being brought to the same temperature as the fatty phase.

Several examples of cosmetic compositions in the form of W/O emulsions will now be given by way of illustration.

EXAMPLE 1

Foundation Cream

| Fatty phase A: | |
|---|---|
| Gelling agent "UNITWAX ®" from the Company United Guardian | 1.5% |
| Alkyldimethicone copolyol "ABIL EM90 ®" from the Company Goldschmidt | 2.5% |
| Isostearyl diglyceryl succinate "IMWITOR 780K ®" from the Company Hüls | 3% |
| Hydrogenated polyisobutene | 2.5% |
| Jojoba oil | 2% |
| Dimethicone "ABIL 10 ®" from the Company Goldschmidt | 5% |
| Cyclomethicone "7158 ®" from the Company Union Carbide | 8% |
| Pigments | 6% |
| Vitamin E | 0.5% |
| Aqueous phase B: | |
| Preserving agents | 0.5% |
| NaCl | 1.1% |
| Glycerol | 2% |
| Spherical silica | 3.5% |
| Water | q.s. for 100% |

This foundation cream is obtained by heating Phases A and B separately to 80° C. and in then gently pouring Phase B into Phase A with vigorous stirring.

The foundation cream obtained has an attractive appearance and has good cosmetic properties.

EXAMPLE 2

Foundation Cream

| Fatty phase A: | |
|---|---|
| Gelling agent "UNITWAX ®" from the Company United Guardian | 1.5% |
| Alkyldimethicone copolyol "Q25200 ®" from the Company Dow Corning | 1% |
| Alkyldimethicone "ABIL EM90 ®" from the Company Goldschmidt | 2% |
| Mineral oil | 2.5% |
| Triglycerides of $C_{10}$–$C_{18}$ fatty acids | 7.5% |
| Tocopherol | 0.1% |
| Cyclomethicone "7158 ®" from the Company Union Carbide | 6% |
| Mixture of dimethicone and dimethiconol "Q2 1403 ®" from the Company Dow Corning | 2.5% |
| Pigments | 6% |
| Aqueous phase B: | |
| Preserving agents | 0.5% |
| Glycerol | 4% |
| $MgSO_4$ | 0.8% |
| Starch powder | 2.5% |
| Water | q.s. for 100% |

This foundation cream is obtained in the same way as in Example 1.

EXAMPLE 3

Cream

| Phase A: | |
|---|---|
| Gelling agent "UNITWIX ®" from the Company United Guardian | 2% |
| Silicone "218-1138 ®" from the Company General Electric | 4% |
| Cyclomethicone "7158 ®" from the Company Union Carbide | 10% |
| Dimethicone "ABIL 10 ®" from the Company Goldschmidt | 10% |
| Phase B: | |
| Preserving agents | 0.5% |
| Glycerol | 2% |
| $MgSO_4$ | 0.8% |
| Water | q.s. for 100% |

This cream is obtained in the same way as described in Example 1.

The cream obtained has a glossy and slightly translucent appearance and has a pleasant, smooth, nonsticky and fresh feel.

EXAMPLE 4

Cream

| Phase A: | |
|---|---|
| Gelling agent "UNITWIX ®" from the Company United Guardian | 2% |
| Dimethicone copolyol "SF 1228 ®" from the Company General Electric | 1.1% |
| Isostearyl diglyceryl succinate "IMWITOR 780K ®" from the Company Hüls | 3% |
| Dimethicone "ABIL 10 ®" from the Company Goldschmidt | 7.5% |
| Cyclomethicone "7158 ®" from the Company Union Carbide | 7.5% |
| Mixture of dimethicone and dimethiconol "Q2 1403 ®" from the Company Dow Corning | 3.5% |
| Phase B: | |
| Preserving agents | 0.5% |
| Glycerol | 4% |
| $MgSO_4$ | 0.7% |
| Bacterial extract "VITACELL ®" from the Company LSN | 5% |
| Water | q.s. for 100% |

This cream is obtained according to the same procedure as described in Example 1.

EXAMPLE 5

Cream

| Phase A: | |
|---|---|
| Gelling agent "UNITWIX ®" from the Company United Guardian | 2% |
| Alkyldimethicone copolyol "ABIL EM90 ®" from the Company Goldschmidt | 2.5% |
| Perfluoropolyether "FOMBLIN HC25 ®" from the Company Montefluos | 1.5% |
| Isostearyl diglyceryl succinate "IMWITOR 780K ®" from the Company Hüls | 3% |
| Trimethylsiloxysilicate | 1.5% |
| Octyl ester of coconut acid | 4% |
| Dimethicone "ABIL 10 ®" from the Company Goldschmidt | 10% |
| Phase B: | |
| Bacterial extract "OXYLASTIL ®" from the Company Sederma | 11% |
| Preserving agents | 0.5% |
| Propylene glycol | 4% |
| NaCl | 1% |
| Water | q.s. for 100% |

The emulsion is obtained in the form of a cream by heating Phase A to 80° C. and then unheated Phase B is slowly added with gentle stirring. Premixing having been carried out, the temperature is brought to 25° C. and then the mixture is vigorously stirred for 10 minutes.

We claim:

1. A cosmetic or pharmaceutical water-in-oil emulsion composition exhibiting time and temperature stability comprising in a non-gelled aqueous phase,
   (a) 15 to 40 weight percent of a fatty phase, said fatty phase comprising
      (i) 10 to 90 percent by weight of a silicone selected from the group consisting of a linear functional polydiorganosiloxane, a linear nonfunctional polydiorganosiloxane, a cyclic polydiorganosiloxane, an alkoxydimethicone, an alkyldimethicone, a phenyldimethicone, a silicone resin and mixtures thereof and
      (ii) 0.1 to 5 percent by weight of a gelling agent comprising a mixture of a glycerol fatty acid ester and a glycol fatty acid ester, present respectively in a ratio of between 75/25 and 95/5 weight percent, said fatty acids being $C_{16}$–$C_{36}$ and at least 50% of said fatty acids being $C_{18}$–$C_{22}$, and (iii) 0.5 to 10 percent by weight of an emulsifying agent selected from the group consisting of an alkyl dimethicone copolyol, an alkoxydimethicone copolyol, a dimethicone copolyol and a mixture thereof.

2. The water-in-oil emulsion composition of claim 1 wherein said emulsifying agent has the formula $$CH_3-\underset{\underset{CH_3}{|}}{\overset{\overset{CH_3}{|}}{Si}}O-\left[\underset{\underset{CH_3}{|}}{\overset{\overset{CH_3}{|}}{Si}}O-\right]_n\left[\underset{\underset{\underset{O-(C_2H_4O)_x(C_3H_6O)_yX}{|}}{(CH_2)_3}}{\overset{\overset{CH_3}{|}}{Si}O}-\right]_m\left[\underset{\underset{Y}{|}}{\overset{\overset{CH_3}{|}}{Si}O}-\right]_q\underset{\underset{CH_3}{|}}{\overset{\overset{CH_3}{|}}{Si}}-CH_3$$

wherein

X represents hydrogen, $C_1$–$C_{16}$ acyl, $C_1$–$C_{16}$ alkoxy or $C_1$–$C_{16}$ alkyl, Y represents $C_8$ to $C_{22}$ alkoxy or $C_8$ to $C_{22}$ alkyl, n=0 to 200, m=1 to 40, and q=0 to 100, the molecular weight of the oxyethylene/oxypropylene groups, $(C_2H_4O-)_x$ $(C_3H_6O-)_y$—X ranging from 250 to 2000, wherein the weight ratio of said oxyethylene to said oxypropylene groups ranges from 100:0 to 20:80.

3. The water-in-oil emulsion composition of claim 1 wherein said emulsifying agent is present in an amount ranging from 2 to 6 percent by weight based on the total weight of said composition.

4. The water-in-oil emulsion composition of claim 1 wherein said linear functional or nonfunctional polydiorganosiloxane has the formula $$X-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_n\underset{\underset{CH_3}{|}}{\overset{\overset{CH_3}{|}}{Si}}-X$$

wherein

X is —$CH_3$ or OH and n equals 0 to 5,000.

5. The water-in-oil emulsion composition of claim 1 wherein said cyclic polydiorganosiloxane has the formula $$\left[\underset{\underset{CH_3}{|}}{\overset{\overset{CH_3}{|}}{Si}}-O\right]_n$$

wherein n is an integer ranging from 3 to 8.

6. The water-in-oil emulsion composition of claim 1 wherein said fatty phase (a) also contains a hydrocarbon oil in an amount ranging from 0.1 to 52 percent by weight based on the total weight of said fatty phase.

7. The water-in-oil emulsion composition of claim 1 further containing an additional emulsifying agent selected from the group consisting of a glycerol ether, a glycerol ester and an oxyethylenated polydimethylsiloxane dispersion in a cyclodimethylsiloxane having an HLB ranging from 2 to 7, said additional emulsifying agent being present in an amount ranging from 0.01 to 5 percent by weight based on the total weight of said emulsifying agent.

8. The water-in-oil emulsion composition of claim 1 wherein said fatty phase (a) also contains a lipophilic U.V. screening agent, a lipophilic vitamin, an antioxidizing agent and a fragrance.

9. The water-in-oil emulsion composition of claim 1 wherein said aqueous phase contains a water-soluble substance selected from the group consisting of a lubricating agent, a hydrating agent, a polysaccharide, an electrolyte and a hydrophilic U.V.screening agent.

10. The water-in-oil emulsion composition of claim 1 wherein said fatty phase also contains a pigment coated with a hydrophilic or hydrophobic substance selected from the group consisting of polyethylene, lecithin, aluminum acylglutamate, poly(methyl methacrylate), triisostearoyltitanate and collagen, said pigment being present in an amount ranging from 0.1 to 15 percent by weight based on the total weight of said composition.

* * * * *